United States Patent [19]

Pospisil

[11] Patent Number: 4,820,151
[45] Date of Patent: Apr. 11, 1989

[54] ORTHODONTIC BRACKET
[75] Inventor: Jirina V. Pospisil, Monrovia, Calif.
[73] Assignee: Unitek Corporation, Monrovia, Calif.
[21] Appl. No.: 47,785
[22] Filed: May 8, 1987
[51] Int. Cl.[4] ............................................. A61C 3/00
[52] U.S. Cl. ........................................ 433/17; 433/8; 433/18
[58] Field of Search ............... 433/17, 8, 16, 18, 19, 433/21

[56] References Cited

U.S. PATENT DOCUMENTS 3,391,461 7/1968 Johnson ................................ 433/17
4,028,809 6/1977 Wallshein ............................. 433/17
4,498,867 2/1985 Kesling ................................ 433/17

OTHER PUBLICATIONS

"American Orthodontics" Bulletin 1-79-3, May 1979, 4 pages (Jim Hilgers Buccal Tubes).

Primary Examiner—John J. Wilson
Attorney, Agent, or Firm—Christie, Parker & Hale

[57] ABSTRACT

A convertible-buccal-tube orthodontic bracket of compact design, and having an auxiliary-appliance hook which is gingivally inclined to prevent occlusal interference.

4 Claims, 2 Drawing Sheets

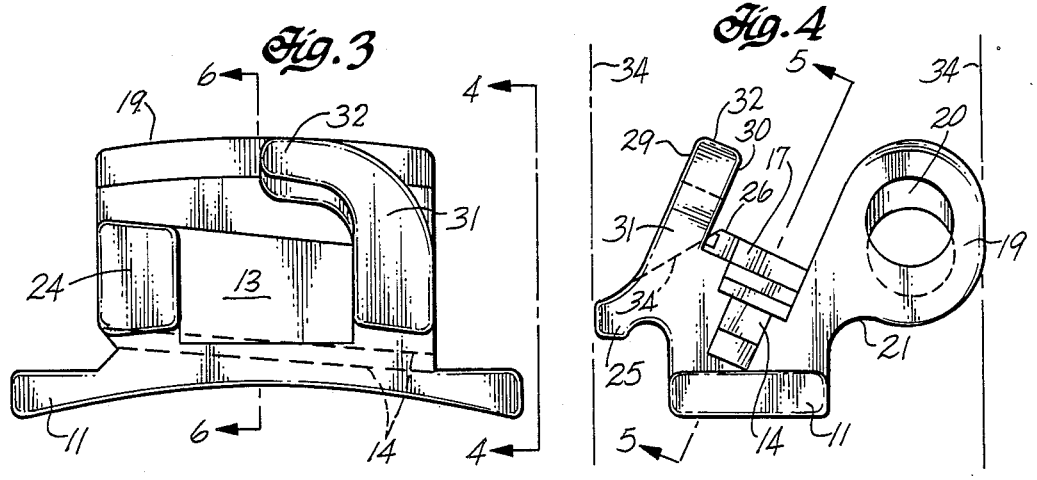
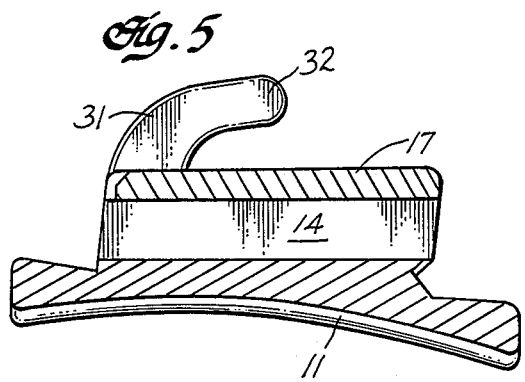
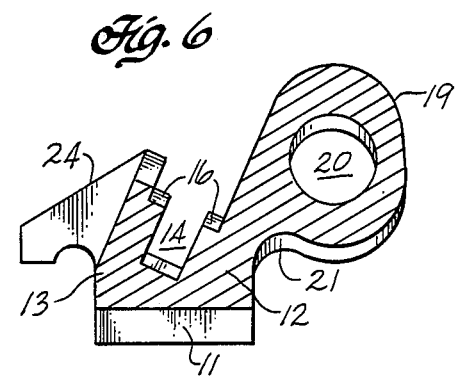

ORTHODONTIC BRACKET

BACKGROUND OF THE INVENTION

This invention relates to a specialized orthodontic bracket intended primarily for use during early treatment phases on lower (mandibular) first molar teeth, and having a convertible arch-wire buccal tube, a second tube for receiving a lip-bumper wire, and an integral hook which is oriented to minimize occlusal interference and to provide an anchorage for elastics, springs, and similar auxiliary appliances.

Convertible molar brackets have been in use for many years, and reference is made to U.S. Pat. No. 3,391,461 for further background information. Brackets of this type are normally used on younger children whose second molars have not yet grown in, but who have fully erupted first molars which serve as anchor teeth for an orthodontic arch wire. The usual rectangular arch-wire slot is covered by a removable cap to provide a terminal buccal-tube anchorage for the arch wire during early treatment.

When the second molars erupt, these newly emerged teeth are provided with banded brackets which take over the "anchor" function and receive the terminal ends of a longer arch wire. Prior to installation of the longer arch wire, the arch-wire cap on each first-molar bracket is removed to enable normal edgewise treatment of the first molars.

It is also known to provide another buccal tube on such molar brackets to receive a facebow tips for the maxillary arch, and the tips of a lip-bumper appliance for the mandibular arch. The facebow is an appliance which is urged distally (rearwardly in the mouth) by extraoral springs or elastics on a headgear or neckband. The lip bumper is a pad fitted between the lower lip and front lower or mandibular teeth, the pad being secured to an arch wire which extends distally to the molar anchor teeth. Natural pressure from the lower lip on the pad results in a rearward force which urges the first molars distally when this kind of corrective tooth movement is needed.

It is desirable to provide a hook on molar brackets for anchorage of auxiliary appliances such as elastic bands. Known molar brackets of this multifunction type, however, are bulky appliances which present a significant problem of occlusal interference, particularly with respect to positioning and extension of the hook. The machined bracket of this invention overcomes such problems by providing all of these functions, while avoiding occlusal interference with a newly positioned low-profile hook.

SUMMARY OF THE INVENTION

The molar bracket of this invention is preferably integrally formed of machined stainless steel, and includes a base of the welding-flange style for attachment to a conventional metal tooth band configured to fit over and be adhesively attached to a molar tooth. The bracket has a body extending generally buccally from the tooth, and the body defines spaced-apart gingival and occlusal portions with parallel facing sidewalls which define therebetween a rectangular arch-wire slot. Preferably, the outer portions of the sidewalls are recessed to define shoulders against which a cap for the arch-wire slot can be secured for subsequent removal as orthodontic treatment progresses. The gingival portion of the bracket body defines a buccal tube.

Means defining an occlusal tie wing are defined on the occlusal portion of the bracket body, and preferably the tie wing means includes spaced-apart mesial and distal tie wings extending occlusally with respect to the base. A hook extends from the occlusal portion in a generally buccal direction, the hook having a base, and an arm projecting distally from the base. Preferably, the hook is an integral extension of the occlusal portion, and has sidewalls which are parallel to the slot-defining sidewall. When the slot is torque angulated, the hook slopes gingivally away from the mesial tie wing to avoid occlusal interference, and the hook is preferably entirely contained between a pair of imaginary parallel buccal-lingually extending planes which respectively contain the outermost gingival and occlusal extremities of the bracket.

BRIEF DESCRIPTION OF THE DRAWINGS

FIG. 3 is a top (toward the gingival) view of the bracket;

FIG. 4 is a mesial-end view of the bracket on lines 4—4 of FIG. 3;

FIG. 5 is a section through the arch-wire slot on lines 5—5 of FIG. 4; and

FIG. 6 is a section on lines 6—6 of FIG. 3.

DESCRIPTION OF THE PREFERRED EMBODIMENT

Figure 1:
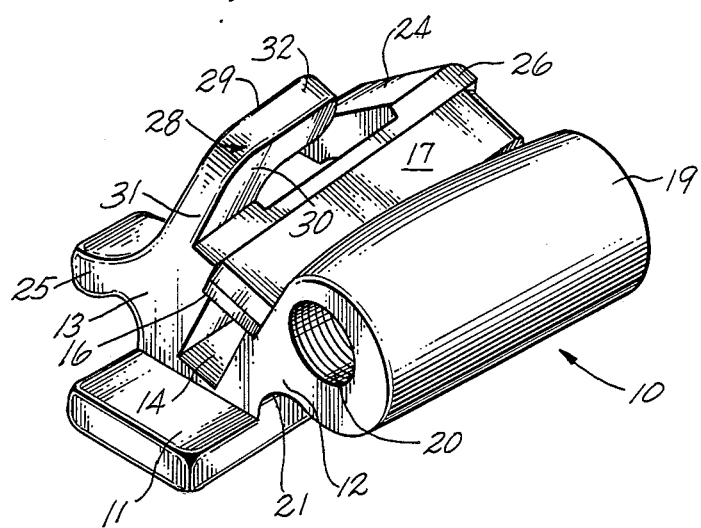
FIG. 1 is a pictorial view of a convertible bracket according to the invention, and with a cap positioned over a rectangular arch-wire slot.

FIG. 1 shows the major features of a mandibular-molar orthodontic bracket 10 constructed according to the invention. The bracket has a conventional welding-flange base 11 which is contoured both mesiodistally and occlusogingivally to match the average curvature of a conventional molar band (not shown) which is cemented to the tooth, and to which the bracket is secured by welding or brazing. A bracket body extends buccally from base 11, and includes a gingival portion 12 and an occlusal portion 13 which are separated to define a rectangular arch-wire slot 14 extending mesiodistally through the bracket. As shown in the drawings, arch-wire slot 14 has significant negative torque angulation (25 degrees is typical), and a lesser distal-offset angulation of about five degrees.

Figure 2:
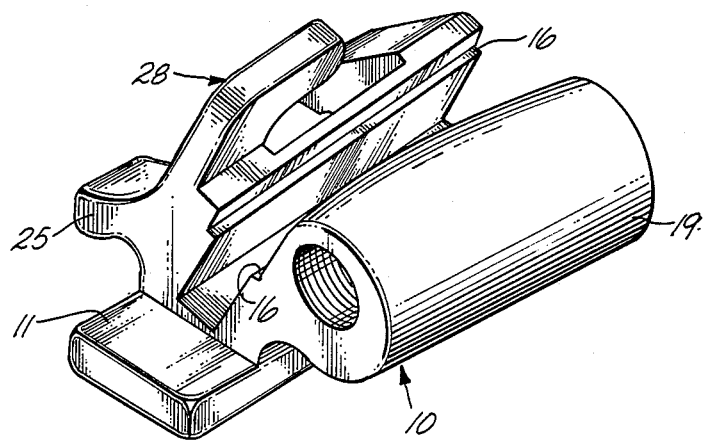
FIG. 2 is a view similar to FIG. 1, but with the cap removed.

Referring to FIGS. 2, 4 and 6, the buccal ends of the sidewalls of arch-wire slot 14 are outwardly stepped to define a pair of shoulders 16 for receiving a thin rectangular slot cap 17 which encloses the slot. The cap is lightly brazed to the bracket body, and is easily stripped off to open the slot (as shown in FIG. 1) so the bracket can be used with the usual edgewise mechanics after eruption of the second molar.

Gingival portion 12 of the bracket body is enlarged to form a lip-bumper buccal tube 19 with a cylindrical passage 20 therethrough. As suggested in FIG. 4, the central axis of passage 20 is preferably slightly inclined with a mesial offset of about five degrees for easy engagement of the lip-bumper end, and for use on a second molar if desired. The band-facing side of the buccal tube has a slight recess 21 which enables the tube to serve as a gingival tie wing for an arch-wire ligature.

Occlusal portion 13 of the bracket extends occlusally to define a pair of recessed and spaced-apart distal and mesial tie wings 24 and 25. These undercut occlusal tie wings are used conventionally in combination with gingival recess 21 of the buccal tube to anchor a ligature wire or elastic band. Distal tie wing 24 terminates buccally in a flat surface 26 parallel to the floor of the arch-wire slot and defining the buccal end of bracket-body occlusal portion 13.

The buccal end of mesial tie wing 25 is smoothly extended to define a distally opening hook 28 with first and second side surfaces 29 and 30, an occlusally extending base 31, and an arm 32 extending distally from base 31 above and generally parallel to the plane of flat surface 26. The hook side surfaces are substantially parallel to the sidewalls of the arch-wire slot, thereby rotating the hook away from occlusal interference, and positioning hook base 31 and arm 32 out of unwanted irritating contact with cheek tissue. As shown in FIG. 4, the hook is entirely contained between two parallel imaginary planes 34 tangent respectively to the gingival and occlusal extremities of the bracket, the planes being perpendicular to the welding tabs of the bracket base.

Preferably, bracket 10 is machined from stainless steel (Type 303 is satisfactory), and is integrally formed with the exception of cap 17 which is a slender stainless-steel tab with slightly bevelled ends as shown in the drawings. The bracket can also be of cast, or made by sintering techniques. A central feature of the new bracket is the low-profile interference-free hook, as combined with overall compactness and multifunctional capability.

What is claimed is:

1. An orthodontic bracket for a molar tooth, comprising:
   a tooth-facing base;
   a bracket body extending from the base, and having spaced-apart occlusal and gingival portions which define therebetween an arch-wire slot, the portions being adapted to receive a cap for closing an outer end of the slot during an initial treatment phase;
   the gingival portion defining a buccal tube with a passage therethrough, and the occlusal portion defining spaced-apart mesial and distal tie wings which cooperate with the buccal tube to provide anchorage for a ligature; and
   a distally opening hook having a base extending generally buccally at a gingival inclination from the occlusal portion, and an arm extending distally from the base, the hook being positioned between a pair of spaced-apart planes which are generally perpendicular to the base and parallel to a longitudinal axis of the arch-wire slot, the planes containing the most occlusally and gingivally extending portion of the bracket;
   the base, body and hook being integrally formed of stainless steel.

2. An orthodontic bracket for a molar tooth, comprising:
   a tooth-facing welding-flange base for attachment to a tooth band;
   a bracket body extending from the base, the body having spaced-apart occlusal and gingival portions with parallel facing sidewalls which define therebetween a rectangular arch-wire slot, the sidewalls being adapted to receive a cap for closing an outer end of the slot during an initial treatment phase;
   the gingival portion defining a buccal tube with a passage therethrough, and the occlusal portion defining a tie-wing means which cooperates with the buccal tube to provide anchorage for a ligature; and
   a distally opening hook with a base on the occlusal portion, and an arm extending distally from the base, the base and arm having generally planar side surfaces which are parallel to the facing sidewalls of the occlusal and gingival portions so the hook extends dominantly buccally and gingivally to avoid occlusal interference when the bracket is mounted on the tooth;
   the base, body and hook being integrally formed of machined stainless steel.

3. The bracket defined in claim 2 wherein sidewalls are inclined gingivally for torque angulation of the arch-wire slot, and the hook correspondingly slopes gingivally away from the tie-wing means.

4. The bracket defined in claim 3 wherein the tie-wing means comprises spaced-apart mesial and distal tie wings, the hook base being secured to and extending from the mesial tie wing.

* * * * *